United States Patent [19]
Schlutow

[11] Patent Number: 5,083,574
[45] Date of Patent: Jan. 28, 1992

[54] SPINAL RESTRAINT APPARATUS

[76] Inventor: Douglas W. Schlutow, 5173 Farm Rd., Waterford, Mich. 48327

[21] Appl. No.: 668,040

[22] Filed: Mar. 12, 1991

[51] Int. Cl.$^5$ ............................................. A61G 1/003
[52] U.S. Cl. ..................................... 128/870; 128/846
[58] Field of Search ............... 128/846, 869, 870, 871, 128/876, 877

[56] References Cited

U.S. PATENT DOCUMENTS

| | | | |
|---|---|---|---|
| 3,526,222 | 9/1970 | Driebelbis | 128/870 |
| 3,889,668 | 6/1975 | Ochs et al. | 128/870 |
| 4,034,748 | 7/1977 | Winner | 128/870 X |
| 4,854,305 | 8/1989 | Bremer | 128/870 X |
| 4,970,739 | 11/1990 | Bradford | 128/870 X |

Primary Examiner—Robert A. Hafer
Assistant Examiner—Sam Rimell
Attorney, Agent, or Firm—Leon Gilden

[57] ABSTRACT

An apparatus wherein a rigid planar board includes a series of slots aligned adjacent opposed edges of the board, wherein a strap system includes a first, second, and third support strap, each orthogonally mounted to a central strap. Each support strap includes a central loop fastener surface, with hook fastener surfaces formed at each end of each strap, wherein each strap is arranged for looping through an associated slot of the board and arranged for securement to the central hook fastener surface of each respective strap. Binding straps are mounted to the second strap to permit interfolding of the straps and subsequent securement of the straps in the interfolded orientation.

3 Claims, 4 Drawing Sheets

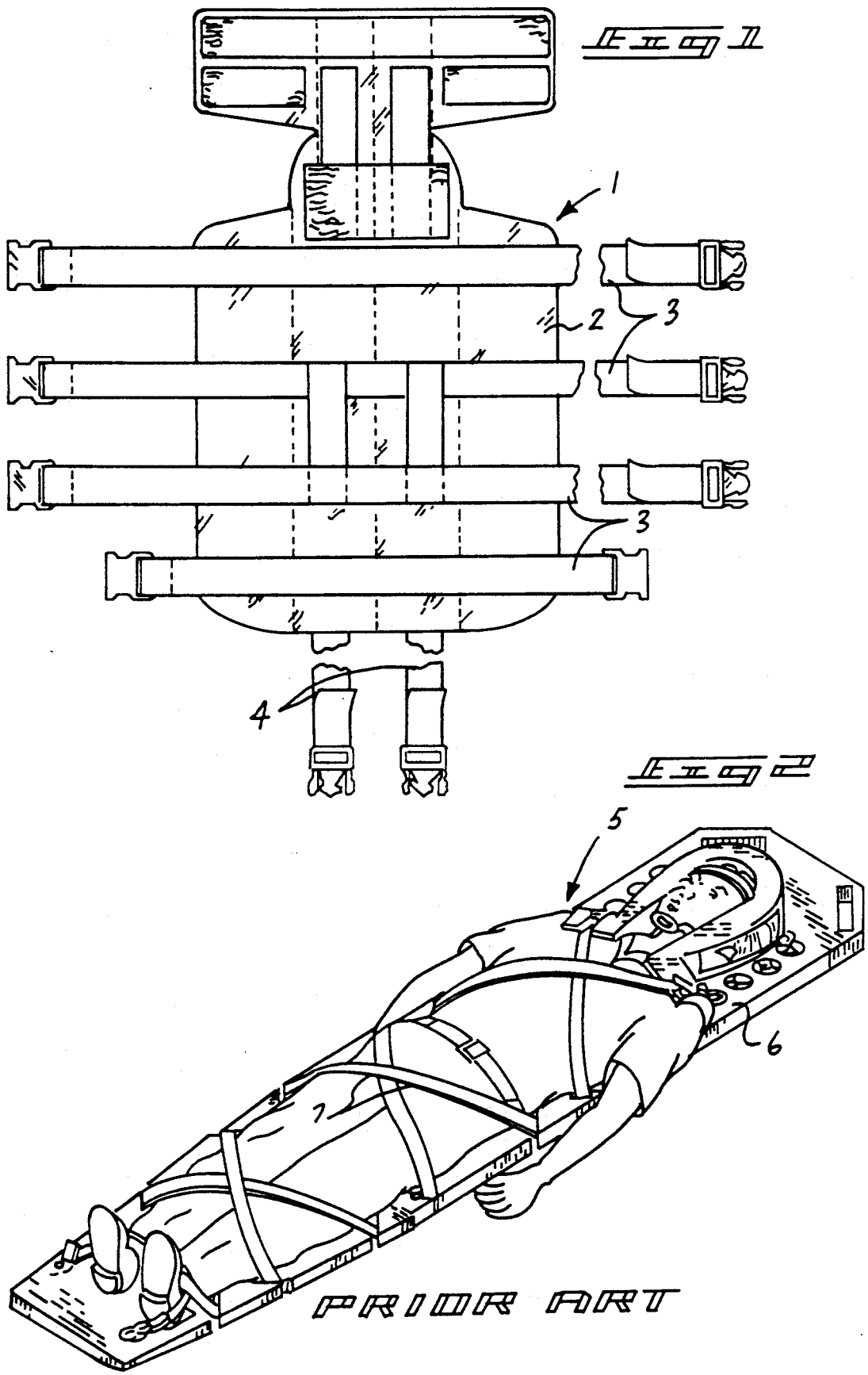

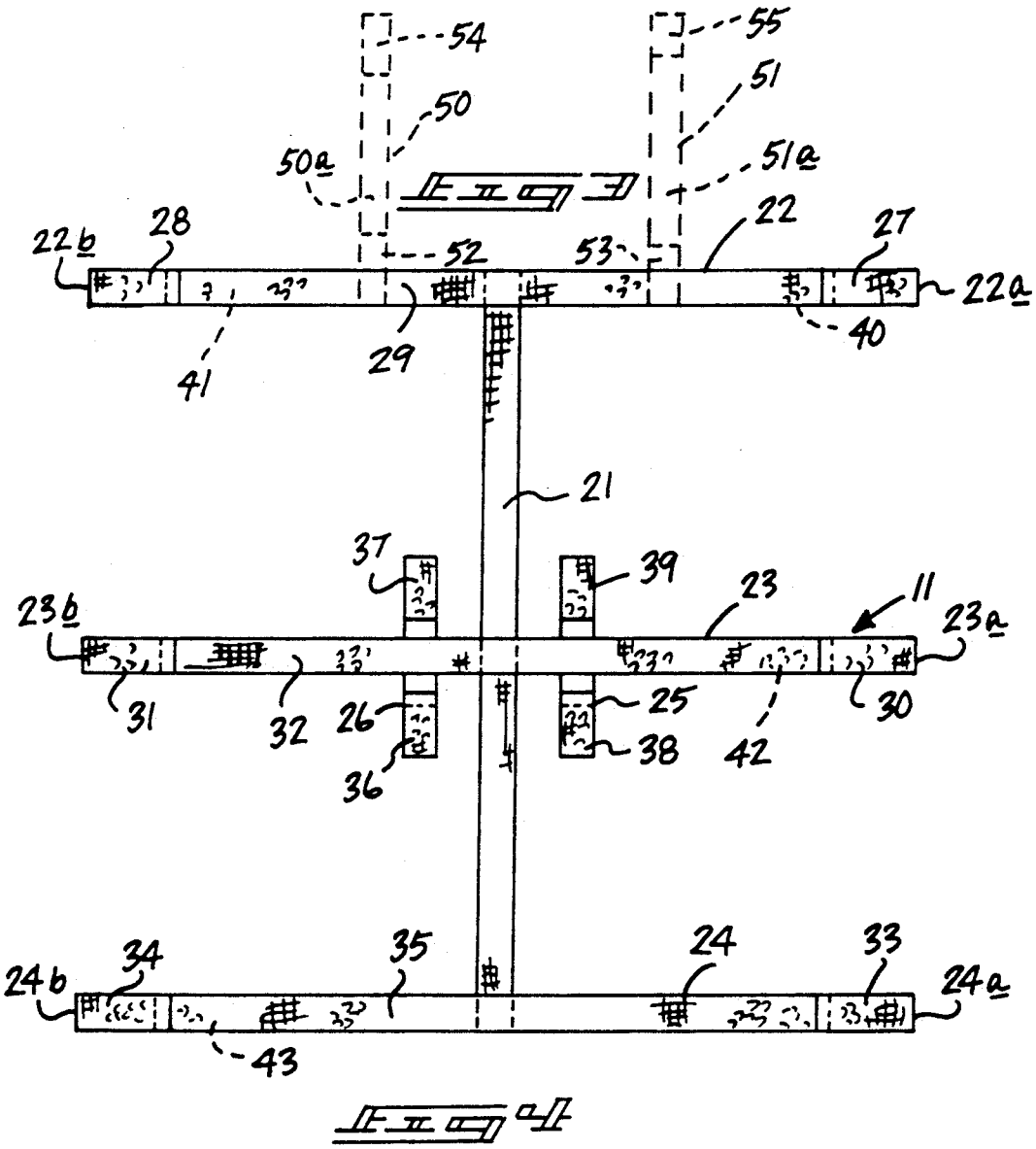
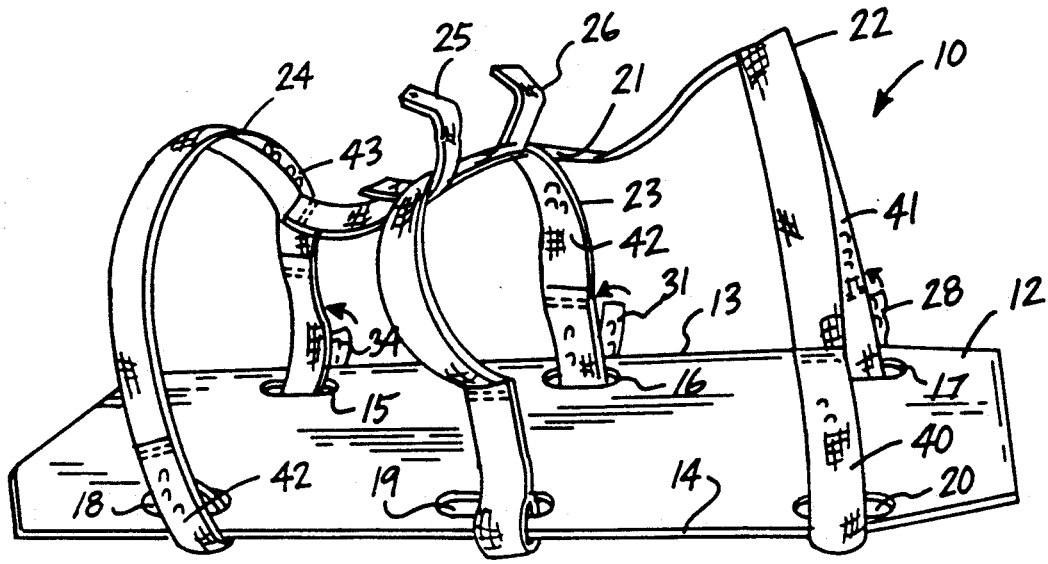

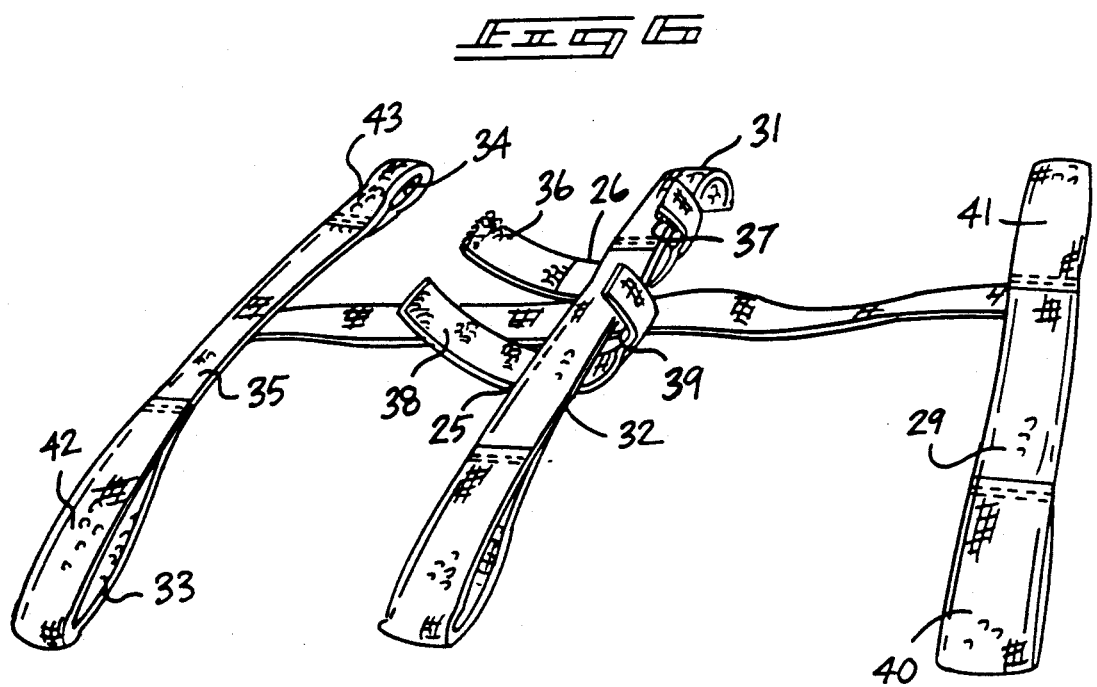
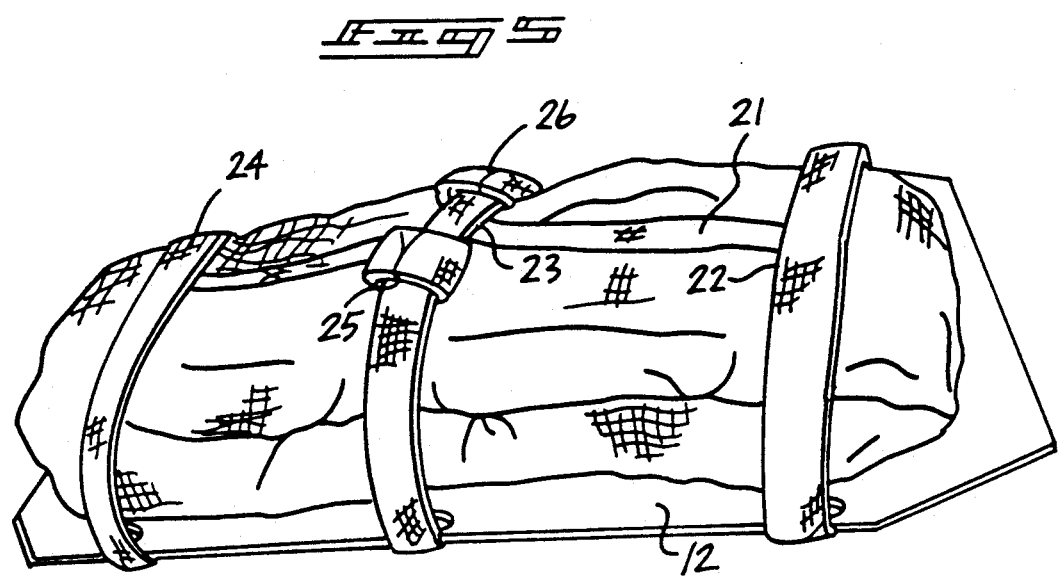

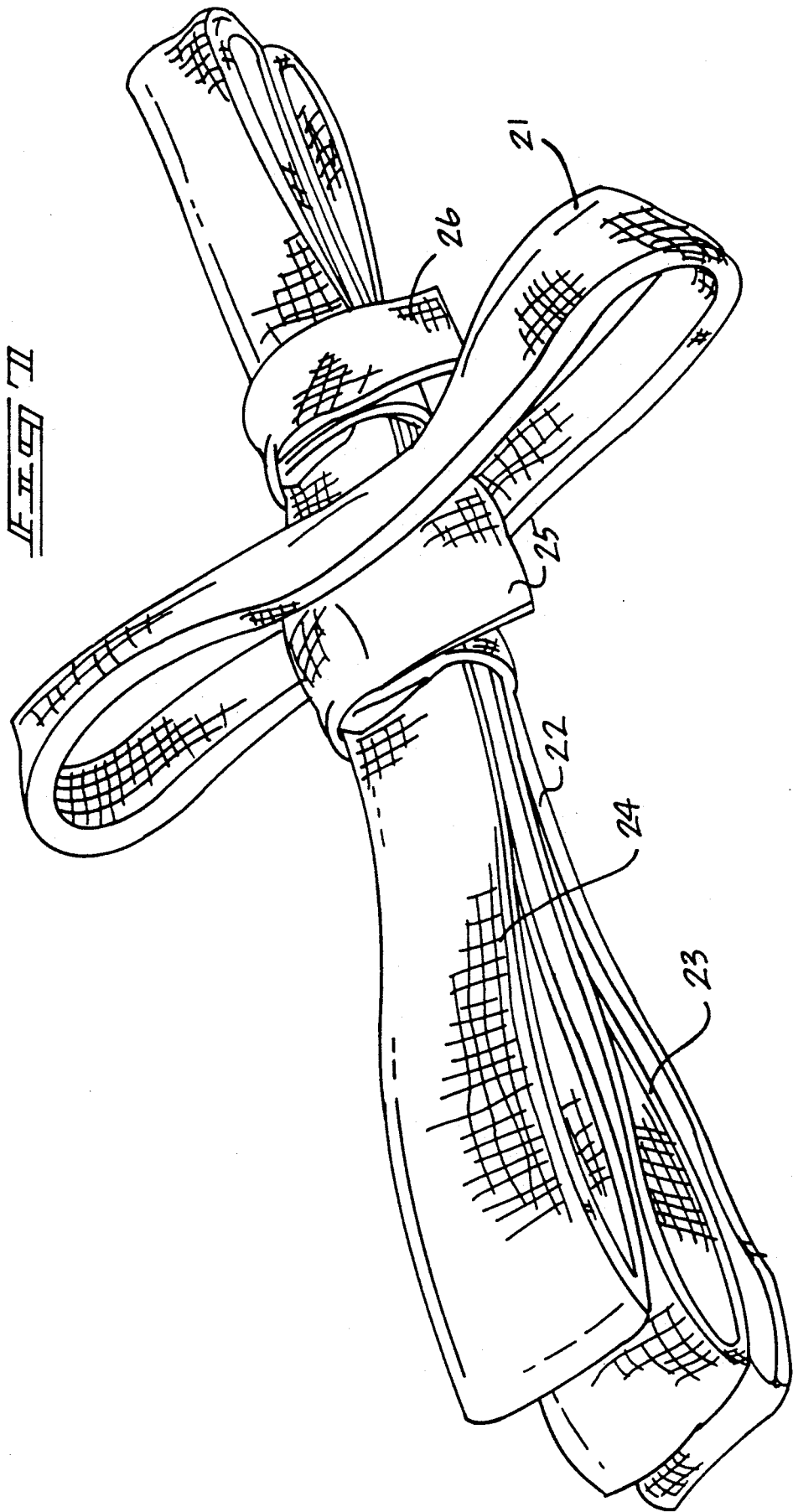

SPINAL RESTRAINT APPARATUS

BACKGROUND OF THE INVENTION

1. Field of the Invention

The field of invention relates to spinal support apparatus, and more particularly pertains to a new and improved spinal restraint apparatus wherein the same permits ease of mounting of a strap system to an associated planar board, with subsequent interfolding of the strap system for ease of transport and storage thereof.

2. Description of the Prior Art

Various restraint apparatus has been provided in the prior art that has been utilized in the positioning and securement of a strap system for positioning a back injury patient upon a support surface. The instant invention attempts to overcome deficiencies of the prior art by providing a spinal restraint system with ease of storage prior and subsequent to use. Examples of the prior art include U.S. Pat. No. 4,655,206 to Moody wherein a planar spinal board mounts a criss-cross of restraint straps to secure a patient therewithin.

U.S. Pat. No. 4,665,908 to Calkin wherein a restraint device is provided with a flexible jacket mounting a matrix of straps for securement of an individual within the jacket structure.

U.S. Pat. No. 4,506,664 to Brault wherein a spine board includes a plurality of strap members mounted to the board in cooperation with a head restraint assembly.

U.S. Pat. No. 4,774,115 to Marchione sets forth a patient mover wherein a framework includes a central web, with carrying straps mounted to the restraining board for transport of a patient thereon.

U.S. Pat. No. 4,566,445 to Jelsma, et al. sets forth a stretcher for traumatized patients, wherein a central board includes a polymeric foam surface, with a plurality of straps mounted underlying the board for securement of the patient thereon.

As such, it may be appreciated that there continues to be need for a new and improved spinal restraint apparatus as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of restrain apparatus now present in the prior art, the present invention provides a spinal restraint apparatus wherein the same permits ease of interfolding of an associated strap system for transport and storage of the system when not in use. As such, the general purpose of the present invention, which will be described subsequently in greater detail, is to provide a new and improved spinal restraint apparatus which has all the advantages of the prior art spinal restraint apparatus and none of the disadvantages.

To attain this, the present invention provides an apparatus wherein a rigid planar board includes a series of slots aligned adjacent opposed edges of the board, wherein a strap system includes a first, second, and third support strap, each orthogonally mounted to a central strap. Each support strap includes a central loop fastener surface, with hook fastener surfaces formed at each end of each strap, wherein each strap is arranged for looping through an associated slot of the board and arranged for securement to the central hook fastener surface of each respective strap. Binding straps are mounted to the second strap to permit interfolding of the straps and subsequent securement of the straps in the interfolded orientation.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other the structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved spinal restraint apparatus which has all the advantages of the prior art spinal restraint apparatus and none of the disadvantages.

It is another object of the present invention to provide a new and improved spinal restraint apparatus which may be easily and efficiently manufactured and marketed.

It is a further object of the present invention to provide a new and improved spinal restraint apparatus which is of a durable and reliable construction.

An even further object of the present invention is to provide a new and improved spinal restraint apparatus which is susceptible of a low cost of manufacture with regard to both materials and labor, and which accordingly is then susceptible of low prices of sale to the consuming public, thereby making such spinal restraint apparatus economically available to the buying public.

Still yet another object of the present invention is to provide a new and improved spinal restraint apparatus which provides in the apparatuses and methods of the prior art some of the advantages thereof, while simultaneously overcoming some of the disadvantages normally associated therewith.

Still another object of the present invention is to provide a new and improved spinal restraint apparatus wherein the same sets forth a matrix of interconnected strap members to define a strap system for ease of securement of the strap system to a spinal board during periods of use and permits ease of interfolding of the strap system during periods of storage and transport.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an orthographic top view of a prior art spinal restraint apparatus.

FIG. 2 is an isometric illustration of a further example of a spinal restraint apparatus.

FIG. 3 is a top orthographic view of the strap system utilized by the instant invention.

FIG. 4 is an isometric illustration of the instant invention.

FIG. 5 is an isometric illustration of the strap system in an initial interfolded orientation.

FIG. 6 is an isometric illustration of the strap system securing a work package therewithin.

FIG. 7 is an isometric illustration of the instant invention setting forth the strap assembly in an interfolded configuration for transport and storage.

DESCRIPTION OF THE PREFERRED EMBODIMENT

With reference now to the drawings, and in particular to FIGS. 1 to 7 thereof, a new and improved spinal restraint apparatus embodying the principles and concepts of the present invention and generally designated by the reference numeral 10 will be described.

FIG. 1 illustrates a prior art spinal restraint apparatus 1, wherein a flexible web 2 mounts horizontal straps 3 and vertical straps 4 to secure a patient therewithin, in a manner as set forth in U.S. Pat. No. 4,665,908. FIG. 2 illustrates a further prior art spinal restraint apparatus 5, as set forth in U.S. Pat. No. 4,655,206, wherein a support board 6 mounts a matrix of crossed webs 7 for securement of a patient to the board member.

More specifically, the spinal restraint apparatus 10 of the instant invention essentially comprises a strap system 11 arranged for mounting to a rigid planar support board 12. The support board 12 includes spaced side edges 13 and 14 coextensively arranged relative to one another relative to the support board 12, with a series of first, second, and third first edge slots 15, 16, and 17 respectively. The first edge slots are spaced adjacent to the first side edge 13, with the second side edge 14 including a series of slots comprising a first, second, and third second edge slot 18, 19, and 20, wherein a respective first, second, and third pairs of slots are arranged in an aligned orientation relative to one another adjacent opposed side edges of the board 12.

The strap system 11 includes a central strap 21. The central strap 21 has fixedly mounted thereto a first support strap 22 orthogonally mounted medially of itself to an upper end of the central strap 21. A second support strap 23 is orthogonally mounted medially of itself and medially of the central strap 21 in an orthogonal relationship. A third support strap 24 is fixedly mounted to a lower terminal end of the central strap 21 medially of itself. The support straps 22 through 24 are of an equal length and are arranged parallel relative to one another, as illustrated. A first and second binding strap 25 and 26 are orthogonally and fixedly mounted to the second support strap medially of themselves and on opposed sides of the central strap 21 and arranged generally parallel to the central strap 21. The binding straps 25 and 26 are of a second length less than those of a first length defined by the support straps 22 through 24. First support strap 22 includes a respective right and left edge 22a and 22b. The support strap 23 includes a right and left edge 23a and 23b, while the third support strap 24 includes a respective right and left edge 24a and 24b. The first support strap includes a first support strap first hook fastener surface 27 and a first support strap second hook fastener surface 28 mounted on the top surface of the first support strap adjacent the respective right and left ends 22a and 22b. A first support strap first loop fastener surface 29 extends coextensively between the first and second hook fastener surfaces 27 and 28. The second support strap 23 includes a first hook fastener surface 30 and a second hook fastener surface 31 mounted on the top surface of the second support strap adjacent the right and left ends 23a and 23b. Similarly, the third strap includes a third support strap first hook fastener surface 33 and a third support strap second fastener surface 34 mounted to the top surface of the third support strap adjacent the right and left ends 24a and 24b, with a third support strap first loop fastener surface 35 extending coextensively between the first and second hook fastener surfaces 33 and 34. The support straps include respective loop fastener surfaces 29, 32, and 35, as noted, extending between the respective hook fastener surfaces. The respective first and second binding straps 25 and 26 each include a respect first binding strap hook fastener surfaces 36 and 38, with respective first and second loop fastener binding surfaces 37 and 39 to permit each binding strap to provide a loop in securing itself in the binding of an individual's arms therethrough, or in the securement of the strap network when in an interfolded configuration, as illustrated in FIG. 7. In use, the first edge of respective first, second, and third slots 15, 16, and 17 receive the respective left third, second, and first ends 24b, 23b, and 22b therethrough, whereupon the respective loop fastener surface of each support strap is securable to each associated central fastener surface, in a manner as illustrated in FIG. 4. Similarly, the first, second, and third right edges are inserted to the respective third, second, and first slots of the second edge defined by slots 20, 19, and 18 and are secured in a similar manner, as illustrated in FIG. 4, to provide a support organization that may be adjusted as required to accommodate individuals of various configurations and sizes. To this end, the first support strap includes a first loop fastener surface 41 formed to a bottom surface of the first support strap adjacent the right and left edges thereof and coextensive of the length of the first strap between the right and left edges 22a and 22b. The second strap includes a second loop fastener surface 42 coextensive between the right and left edges 23a and 23b coextensive of the bottom surface of the second strap, and a third loop fastener surface 43 is mounted coextensively of the third strap coextensive of its length and surface between the respective right and left edges 24a and 24b.

Further, respective right and left shoulder straps 51 and 50 are orthogonally mounted to the first strap 22 on opposed sides of its intersection with the strap 21. A respective left and right securement loop 52 and 53 are provided and may be secured about the first strap 22 by conventional hook and loop fastening surfaces, wherein a shoulder strap left and right upper hook fastener surface 54 and 55 is mounted to a top surface of the left and right straps 50 and 51 about an upper portion thereof. A respective left and right loop fastener surface 50a and 51a is mounted between the hook fastener surfaces 54 and 55 and each securement loops 52 and 53.

Further, with reference to FIG. 3, the second and third straps 23 and 24 respectively may be formed of a lesser length than that of the first strap 22, while maintaining the parallel relationship. Such tapering of the straps toward the third strap 24 or the foot strap would permit ease of visual orientation of the strap system for use in emergency and field situations as required, while maintaining the positioning of the various hook and loop fastener surfaces for mounting to the support board 12 for its proper orientation about an individual.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A spinal restraint apparatus comprising, in combination,
    a rigid planar support board, the support board including a first side edge spaced from and coextensive with a second side edge, the first side edge including a first edge first slot, a first edge second slot, and a first edge third slot, and the second edge including a second edge first slot, a second edge second slot, and a second edge third slot, and
    a strap system including a first strap, a second strap, and a third strap, wherein the first strap includes a first strap right end edge and a first strap left end edge, the second strap includes a second strap right end edge and a second left end edge, and the third strap includes a third strap right end edge and a third strap left end edge, and
    wherein the first strap, second strap, and third strap are each defined by a predetermined length and are arranged coextensively and parallel relative to one another, and
    a central strap orthogonally oriented relative to the first strap, second strap, and third strap, and medially bisecting the first strap, second strap, and third strap, and the first strap left end edge and the first strap right end edge are directed through the respective first edge first slot and second edge first slot respectively, and
    the second strap left end edge and the second strap right end edge are directed through the first edge second slot and second edge second slots respectively, and
    the third strap left end edge and the third strap right end edge are directed through the first edge third slot and the second edge third slot respectively, and
    securement means mounted to each strap to permit securement of each strap to the support board, and wherein the securement means includes a a first strap first hook fastener surface mounted to a first top surface of the first strap adjacent the first strap right end edge, and a first strap second hook fastener surface mounted to the first top surface adjacent the first strap left end edge, and a first strap first loop fastener surface extending between the first strap first hook fastener surface and the first strap second hook fastener surface, and a second strap first hook fastener surface mounted to a second top surface defined by the second strap adjacent the second strap right end edge, and a second strap second hook fastener surface mounted to the second top surface adjacent the second strap left end edge, and a second strap first loop fastener surface extending between the second strap first hook fastener surface and the second strap second hook fastener surface, and the third strap defining a third top surface, with a third strap first hook fastener surface formed to the third top surface adjacent to the third strap right end edge, and a third strap second hook fastener surface mounted to the third top surface adjacent the third strap left end edge, and a third strap first loop fastener surface formed to the third top surface coextensively between the third strap first hook fastener surface and the third strap second hook fastener surface, and including a first binding strap orthogonally mounted to the second strap between the second strap right end edge and the central strap, and a second binding strap orthogonally mounted to the second strap between the central strap and the second strap left end edge, and the first binding strap including a first binding strap hook fastener surface and a first binding strap loop fastener surface to permit securement of the first binding strap about an individual's left arm, and the second binding strap including a second binding strap hook fastener surface and a second binding strap loop fastener surface to permit securement of the second binding strap about an individual's right arm when an individual is mounted on the support board underlying the strap system.

2. An apparatus as set forth in claim 1 wherein the first strap includes a first bottom surface opposed to the first top surface, the second strap is defined by a second bottom surface opposed to the second top surface, and the third strap is defined by a third bottom surface opposed to the third top surface, and securement means further includes a first support strap second loop fastener surface mounted to the first bottom surface coextensive therewith, the second strap including a second strap second loop fastener surface mounted coextensively to the second bottom surface, and the third strap including a third strap third loop fastener surface coextensively mounted to the third bottom surface adjacent the third strap.

3. An apparatus as set forth in claim 2 including a right shoulder strap and a left shoulder strap orthogonally mounted to the first strap on opposed sides with a central strap, with the right shoulder strap including a right shoulder strap surface extending from the first strap and including a first hook fastener surface mounted to the right shoulder strap between the right shoulder strap loop fastener surface and the right shoulder strap hook fastener surface, and the left shoulder strap including a left shoulder strap loop fastener surface mounted to a top surface of the left shoulder strap, and including a left shoulder strap hook fastener surface formed to the left shoulder strap top surface between the left shoulder strap loop fastener surface and an outer edge of the left shoulder strap.

* * * * *